(12) United States Patent
Myers et al.

(10) Patent No.: US 12,047,717 B2
(45) Date of Patent: *Jul. 23, 2024

(54) WARM WHITE LIGHT ILLUMINATION AND DIGITAL IMAGE PROCESSING OF DIGITAL IMAGES DURING MICROSURGERY

(71) Applicant: Alcon Inc., Fribourg (CH)

(72) Inventors: Gillian Myers, Santa Barbara, CA (US); Alan Fridman, Goleta, CA (US); Maximiliano Ramirez Luna, Santa Barbara, CA (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/464,661

(22) Filed: Sep. 11, 2023

(65) Prior Publication Data

US 2023/0421737 A1 Dec. 28, 2023

Related U.S. Application Data

(63) Continuation of application No. 17/659,124, filed on Apr. 13, 2022, now Pat. No. 11,792,376.

(60) Provisional application No. 63/209,523, filed on Jun. 11, 2021.

(51) Int. Cl.
| | |
|---|---|
| *H04N 9/64* | (2023.01) |
| *A61B 3/00* | (2006.01) |
| *A61B 3/13* | (2006.01) |
| *A61B 3/14* | (2006.01) |
| *H04N 23/88* | (2023.01) |

(52) U.S. Cl.
CPC ........... *H04N 9/646* (2013.01); *A61B 3/0008* (2013.01); *A61B 3/0041* (2013.01); *A61B 3/13* (2013.01); *A61B 3/145* (2013.01); *H04N 23/88* (2023.01)

(58) Field of Classification Search
CPC .......... H04N 9/646; H04N 23/88; A61B 3/13; A61B 3/0008; A61B 3/00; A61B 3/145; A61B 3/0041; G02B 21/0012; G02B 21/365
USPC ...... 348/46, 78, 572; 382/103; 600/356, 236
See application file for complete search history.

(56) References Cited

U.S. PATENT DOCUMENTS

2015/0077528 A1* 3/2015 Awdeh ................... A61B 3/14
348/78

* cited by examiner

*Primary Examiner* — Sherrie Hsia
(74) *Attorney, Agent, or Firm* — Quinn IP Law

(57) ABSTRACT

A method for enhancing digital images during a microsurgery, e.g., an eye surgery, includes collecting digital images of target anatomy using a digital camera as the target anatomy is illuminated by warm white light. The method includes identifying, via a processor in communication with the digital camera, a predetermined stage of the microsurgery. Within the images, the processor digitally isolates a first pixel region, e.g., a pupil pixel region, from a second pixel region, e.g., an iris pixel region, and adjusts a characteristic of constituent pixels thereof. The method, possibly recorded as instructions in a computer-readable medium, may be used to enhance a red reflex at predetermined stages of an eye surgery. A system includes a lighting source for emitting warm white light having a color temperature of less than about 4000° K, the camera, and the processor.

20 Claims, 4 Drawing Sheets

WARM WHITE LIGHT ILLUMINATION AND DIGITAL IMAGE PROCESSING OF DIGITAL IMAGES DURING MICROSURGERY

CROSS-REFERENCE TO RELATED APPLICATIONS

This application is a Continuation of U.S. patent application Ser. No. 17/659,124, filed Apr. 13, 2022, which claims priority to and the benefit and the benefit of U.S. Provisional Patent Application Ser. No. 63/209,523, filed Jun. 11, 2021, both of which are hereby incorporated by reference in their entireties.

TECHNICAL FIELD

The present disclosure generally relates to automated methodologies and related hardware and software system-based digital image processing solutions for collecting and processing digital images of target anatomy of a human patient when the target anatomy is illuminated with warm white light.

BACKGROUND

Modern microsurgery involves the use of a wide range of task-specific precision surgical tools, each of which a surgeon manipulates within a surgical scene. Magnified stereoscopic images of the surgical scene and target anatomy are often displayed within an operating suite using one or more high-resolution display screens. Digital presentation of magnified images of the target anatomy enables attending clinicians to properly visualize the surgical scene when performing a given surgical task.

Visualization of a surgical scene requires adequate task lighting. Surgical task lighting is task-specific, with lighting devices possibly including any or all of a microscope-mounted lighting source, an overhead surgical lighting arrays, a surgeon-worn headlight, or an endoilluminator or light wand. Each lighting device emits light having a particular wavelength range and corresponding color temperature. Thus, task illumination is often followed by digital image processing in order to present a more realistic representation of the target anatomy via the display screens and optics used within the operating suite.

SUMMARY

Disclosed herein are methods and accompanying systems and software solutions for selectively enhancing digital images that are collected in real time during microsurgery using warm white light illumination. Due to the benefits of minimizing exposure of the human eye to blue wavelength light, the various embodiments described herein relate to surgeries of the eye, primarily including but not limited to cataracts surgery, lens replacement, and other procedures benefitting from detection and analysis of the eye's natural red reflex. However, those skilled in the art will appreciate that other microsurgeries seeking to limit blue light exposure of a given target anatomy may benefit from the disclosed solutions.

In a particular embodiment, a method for enhancing digital images during microsurgery includes collecting digital images of target anatomy of a human patient during the microsurgery. This occurs by operation of a digital camera as the target anatomy is illuminated by warm white light. The method in this embodiment also includes identifying a predetermined stage of the microsurgery via a processor in wired or wireless communication with the digital camera. Within the digital images, operation of the processor isolates a first pixel region from a second pixel region, e.g., a pupil pixel region from a surrounding iris pixel region in a representative eye surgery, and then adjusts a characteristic of constituent pixels comprising the first or second pixel region. Images with the adjusted characteristic, i.e., adjusted images, are then presented or displayed via one or more display screens.

A system is also disclosed herein for enhancing digital images during the above-noted eye surgery. The system may include a lighting source, such as a microscope-mounted lamp, as well as a digital camera and the above-noted processor, with the processor being in communication with or integrated with the digital camera and lamp. The lighting source is operable for directing warm white light onto/into a target eye. The digital camera is operable for collecting digital images of the target eye as the eye is illuminated by the warm white light.

In an exemplary configuration of the system, the processor detects a predetermined stage of the eye surgery, as one requiring an enhanced red reflex of the target eye. Non-limiting representative stages of surgery during cataracts surgery, for instance, include incision, lens insertion, and lens removal. The processor in this embodiment tracks motion of the target eye, e.g., using the digital camera and motion tracking logic. Within the digital images of the target eye during the predetermined stage of the eye surgery, the processor digitally isolates a pupil pixel region from an iris pixel region surrounding the pupil pixel region, and adjusts a characteristic of constituent pixels comprising the pupil pixel region or the iris pixel region to thereby generate adjusted images. The adjusted images as provided herein have the enhanced red reflex. The processor is also operable for outputting a video display control signal to at least one display screen to cause the screen(s) to display the adjusted images during the predetermined stage of the eye surgery.

Another aspect of the subject disclosure includes a computer-readable medium on which is recorded instructions for enhancing the red reflex during a representative eye surgery. Execution of the instructions by a processor of the processor in this instance causes the processor to perform logical blocks or sequences of the present method as described in detail in the following disclosure.

The above-described features and advantages and other possible features and advantages of the present disclosure will be apparent from the following detailed description of the best modes for carrying out the disclosure when taken in connection with the accompanying drawings.

BRIEF DESCRIPTION OF THE DRAWINGS

The drawings described herein are for illustrative purposes only, are schematic in nature, and are intended to be exemplary rather than to limit the scope of the disclosure.

Figure 1:
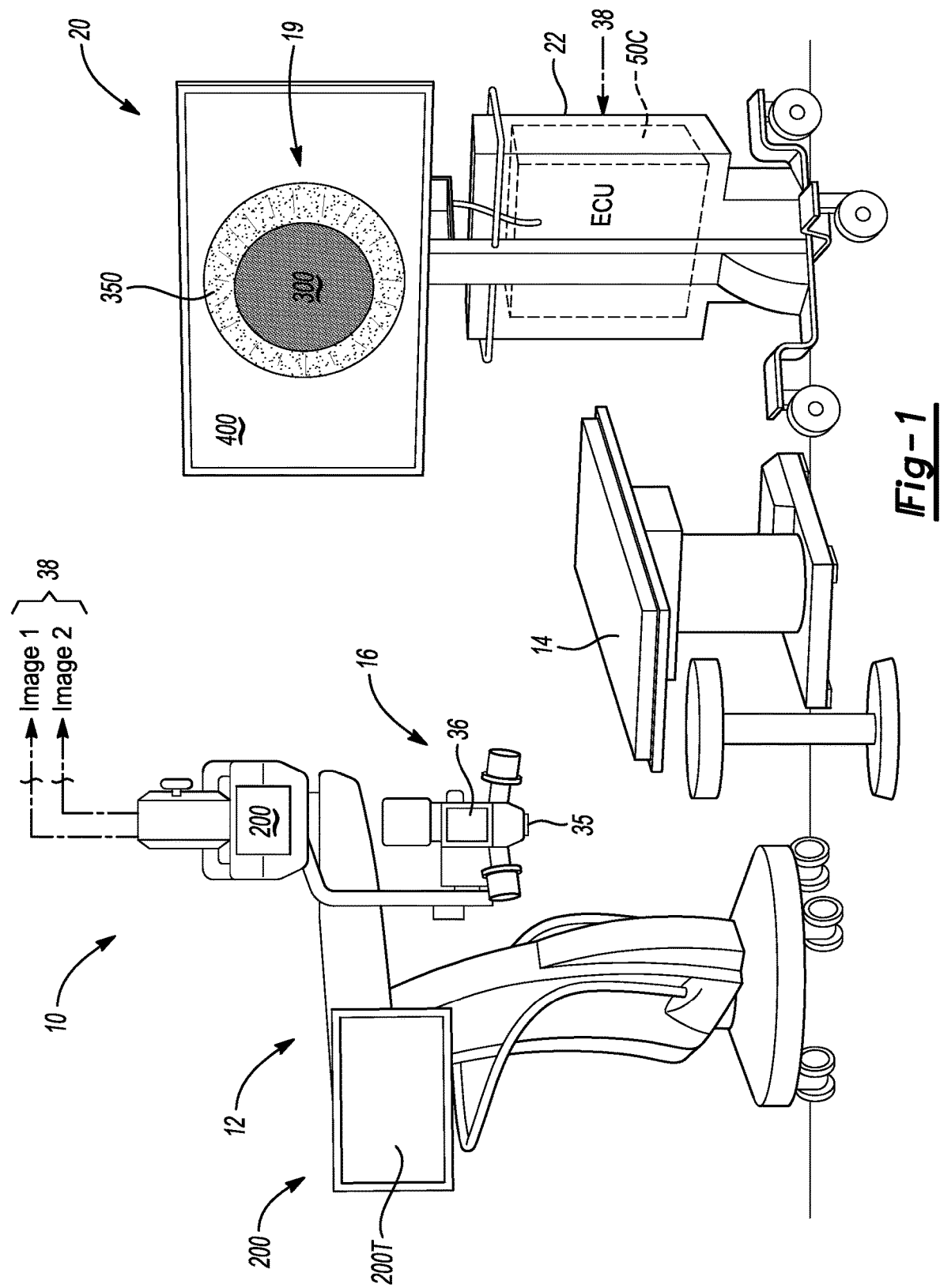
FIG. 1 illustrates a representative operating suite using a processor configured to execute instructions embodying a method in accordance with the subject disclosure.

The above summary is not intended to represent every possible embodiment or every aspect of the subject disclosure. Rather, the foregoing summary is intended to exemplify some of the novel aspects and features disclosed herein. The above features and advantages, and other features and advantages of the subject disclosure, will be readily apparent from the following detailed description of representative embodiments and modes for carrying out the subject disclosure when taken in connection with the accompanying drawings and the appended claims.

DETAILED DESCRIPTION

Embodiments of the present disclosure are described herein. It is to be understood, however, that the disclosed embodiments are merely examples and other embodiments can take various and alternative forms. The figures are not necessarily to scale. Some features could be exaggerated or minimized to show details of particular components. Therefore, specific structural and functional details disclosed herein are not to be interpreted as limiting, but merely as a representative basis for teaching one skilled in the art to variously employ the present disclosure.

As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Certain terminology may be used in the following description for the purpose of reference only, and thus are not intended to be limiting. For example, terms such as "above" and "below" refer to directions in the drawings to which reference is made. Terms such as "front," "back," "fore," "aft," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

As appreciated in the art, the term "full spectrum light" describes the full wavelength range of human-visible light, conventionally defined as 380 nanometers (nm) to 700 nm. In addition to wavelength, visible light is often described in terms of color temperature using descriptions such as "warm white light", "daylight white light", and "cool white light". Color temperature is expressed in degrees Kelvin (° K), with warm white light in particular typically referring to light having a color temperature of less than about 4000° K. Such light falls predominantly within the orange and red ranges of full spectrum light. In contrast to warm white light, cool white light has a higher color temperature of about 5500° K to 7000° K or more, and is often dominated by blue light. Daylight white light falls somewhere between the conventionally defined color temperature limits of warm white light and cool white light.

Medical grade microscopes are used in the performance of microsurgery to help a surgeon accurately visualize the relevant target anatomy. For instance, ophthalmic microscopes and associated high-resolution imaging software enable ophthalmologists to accurately visualize the interior and exterior anatomy of a target eye. Such microscopes are equipped to illuminate and image the eye. This often occurs using full spectrum light or daylight white light in order to produce natural looking real-life images.

However, full spectrum and daylight white light contain high levels of blue light, i.e., light energy having a wavelength falling within the 380 nm to 450 nm range. Prolonged exposure to blue light poses a phototoxicity risk to exposed tissue, principally to exposed and irradiated surfaces of the cornea, retina, and lens. Such exposure can lead to increased patient recovery time, post-surgical discomfort, and cellular damage. The present solutions are therefore directed to minimizing blue light exposure while taking advantage of properties of warm white light in other ways, such as by selectively enhancing the red reflex response of a target eye during a representative eye surgery as described below.

Referring now to the drawings, wherein like reference numbers refer to like components, an operating suite 10 is depicted schematically in FIG. 1 as it may appear during a representative microsurgery. As appreciated by those skilled in the art, the operating suite 10 may be equipped with a multi-axis surgical robot 12 and an operating platform 14. The surgical robot 12 may be connected to a microscope 16, shown in FIG. 1 as a digital ophthalmic microscope, through which a surgeon is able to view a patient's target anatomy under high levels of magnification. A lighting source 35 and a digital camera 36 may be coupled to or integral with the microscope 16. For example, using associated hardware and software, the surgeon using the microscope 16 is able to view highly magnified enhanced digital images 19 of the target anatomy. Visualization is facilitated via one or more high-resolution display screens 20 and 200, any or all of which may include a touch screen 200T, e.g., a capacitive display surface. As shown, the enhanced digital images 19 are of a representative target eye 30 (see FIG. 2), with the images 19 in FIG. 1 including a pupil 300, surrounding iris 350, and portions of the sclera 400.

Figure 2:
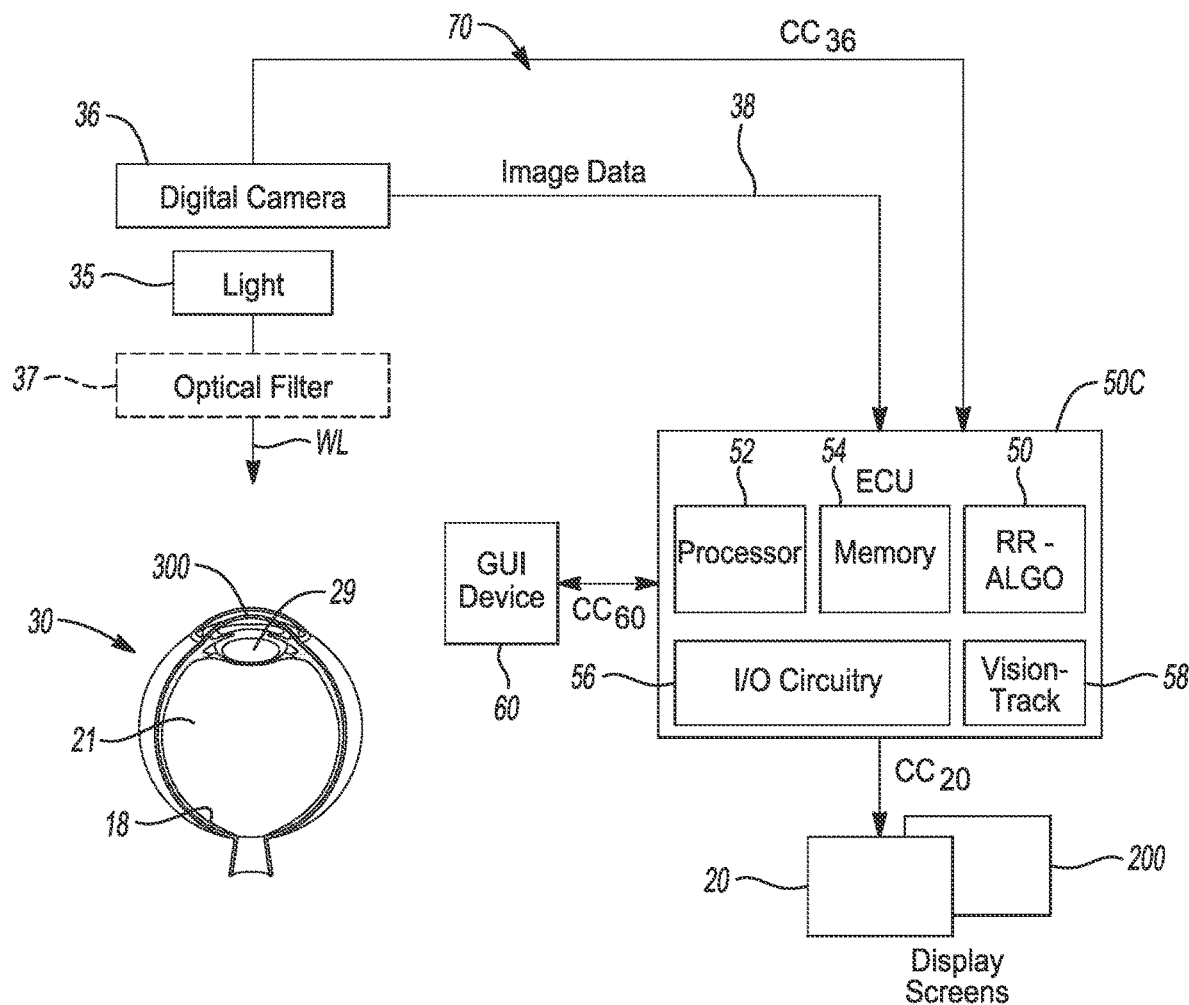
FIG. 2 is a schematic illustration of the processor shown in FIG. 1 in a non-limiting embodiment in which the processor is part of an electronic control unit (ECU), with associated signal processing during an exemplary eye surgery.

Also present within the operating suite 10 is a cabinet 22 containing an electronic control unit (ECU) 50C, a processor 52 of which is shown in FIG. 2. The ECU as depicted may be housed within the cabinet 22 in a possible implementation. Other embodiments are described below in which the processor 52 is integrated with or into other hardware within the operating suite 10 apart from the cabinet 22, and therefore the illustrated implementation of FIG. 1 is non-limiting and exemplary, with the relevant processing functions of the ECU 50C and the processor 52 described interchangeably below without regard to the particular location of either device.

Figure 3:
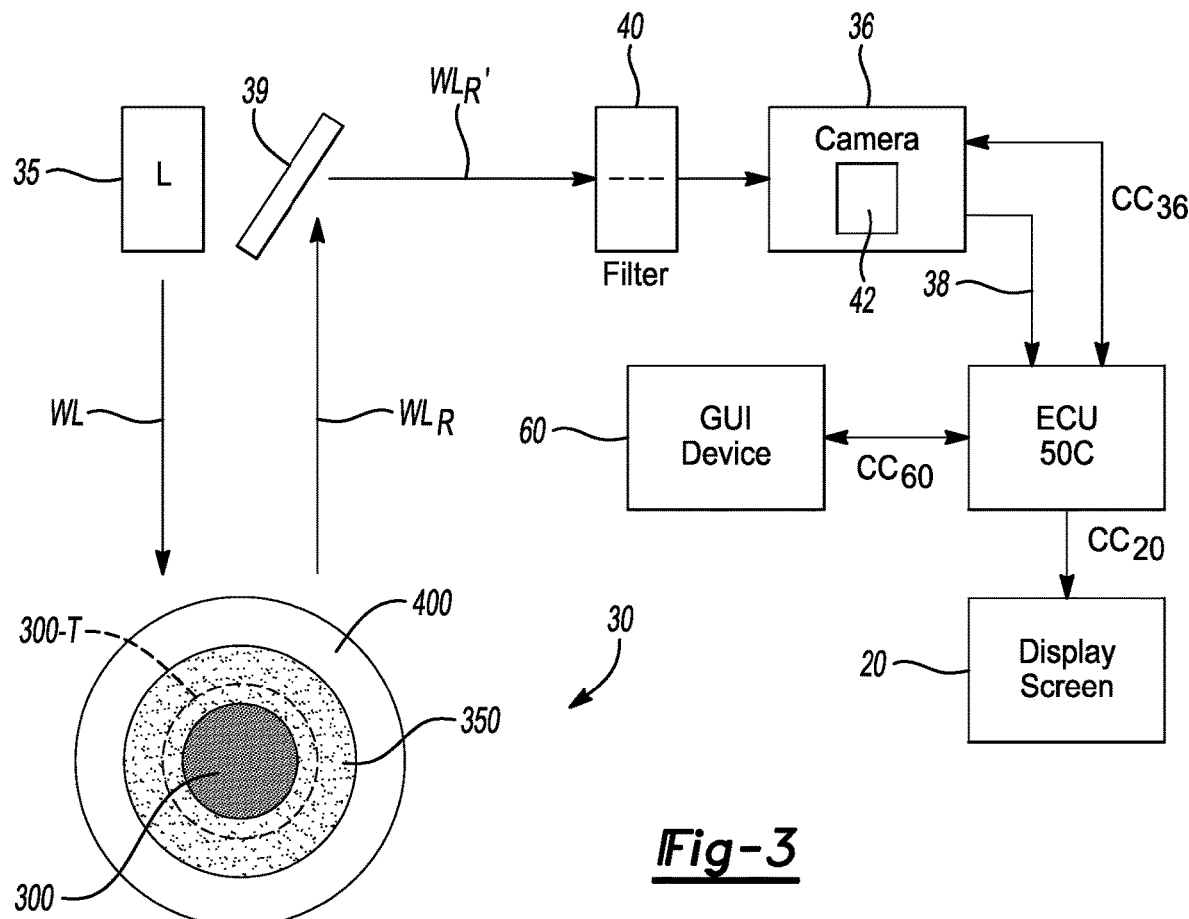
FIG. 3 is a schematic illustration of a system for enhancing the red reflex and limiting blue light exposure during the representative eye surgery of FIG. 2.

The ECU 50C is configured to receive digital image data (arrow 38), possibly stereoscopic images as represented in FIG. 1 by arrows "Image 1" and "Image 2". While collecting the digital image data (arrow 38), the ECU 50C executes instructions embodying a method 50, an example of which is described below with reference to FIG. 5. The ECU 50C is used as part of a system 70, components of which are depicted in FIGS. 2 and 3, with the system 70 in some embodiments being operable for selectively enhancing the red reflex response ("red reflex") of a target eye 30 (see FIGS. 2 and 3). Red reflex enhancement is performed in accordance with the subject disclosure automatically or in response to commands of the surgeon in different embodiments. Moreover, red reflex enhancement may be restricted within the scope of the disclosure only to predetermined stages of the eye surgery when detection and evaluation of the red reflex by the surgeon would be informative, e.g., when making an incision or when removing or inserting an intraocular lens in an exemplary eye surgery.

With respect to the red reflex, during cataract surgery and certain other ophthalmic procedures, a surgeon may wish to detect and evaluate the eye's reflective performance in response to incident light. The term "red reflex" thus refers to a detectable reflective phenomenon that normally occurs when light enters the pupil 300 and reflects off of the retina 18 at the posterior of the vitreous cavity 23, both of which are shown in FIG. 2, with a characteristic red hue. Red reflex tests are frequently used by eye surgeons and other clinicians to detect possible abnormalities of the eye's posterior anatomy. Also detectable via red reflex tests are opacities located along the optical axis 11, likewise shown in FIG. 2 along with the pupil 300 and a lens 29. Such opacities are often present due to cataracts, for example, with cataracts leading to a progressive clouding of the lens 29. Other possible causes of a poor red reflex include corneal scarring and vitreous hemorrhage. The absence of a proper red reflex response is therefore of interest to a surgeon when diagnosing or treating various ocular conditions.

Figure 5:
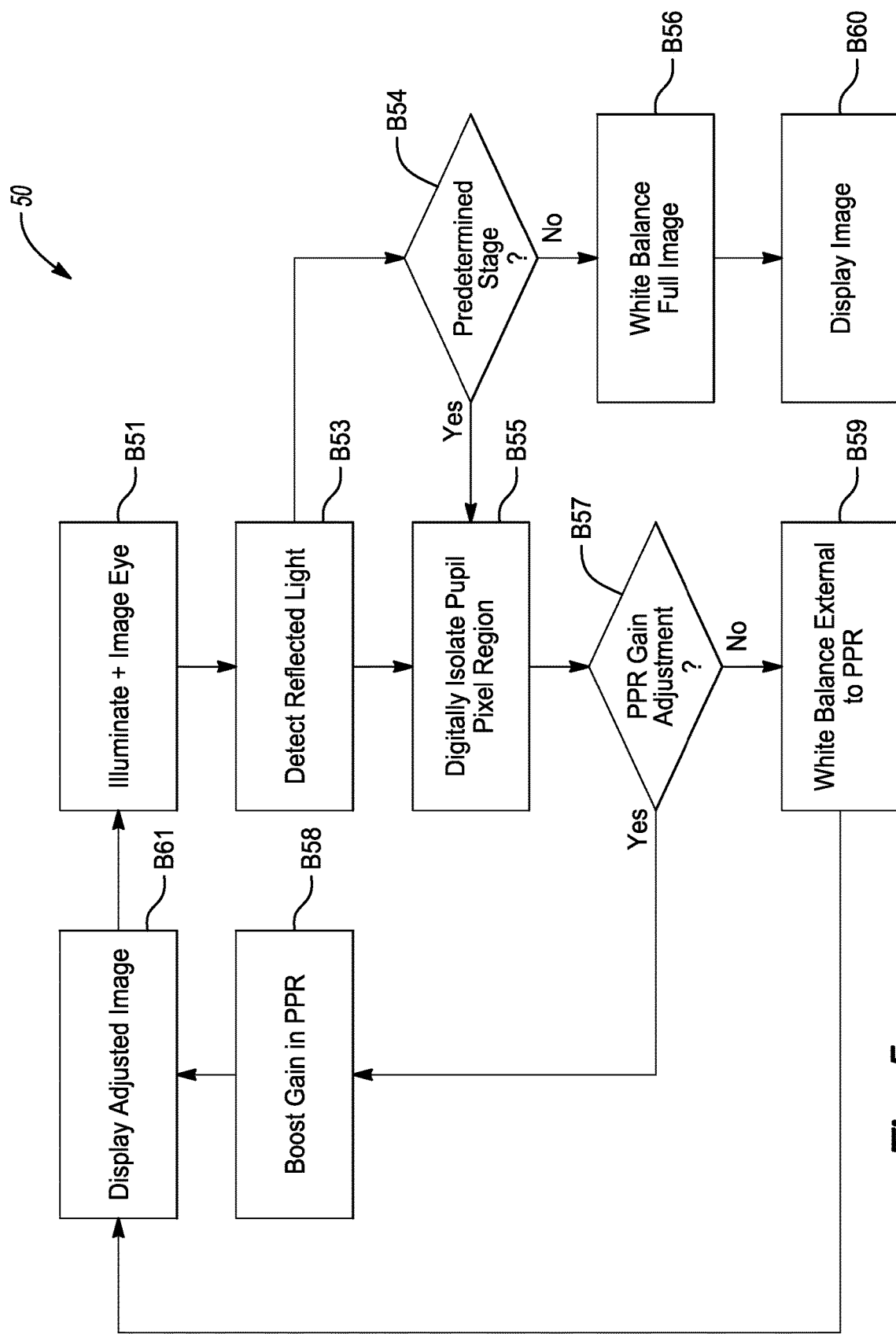
FIG. 5 is a flow chart describing a method for digitally enhancing images collected under warm white light illumination conditions in accordance with the disclosure.

Within this established exemplary use context, the ECU 50C depicted in FIG. 1 is programmed with instructions or computer-executable code embodying an algorithm, which in turn is executed to perform the method 50 of FIG. 5. When performing the present method 50, the ECU 50C seamlessly presents enhanced digital images 19 via the display screens 20 and/or 200. That is, digital image processing functions are performed by the ECU 50C in an unobtrusive and transparent manner from the perspective of the surgeon, so that the enhanced digital images 19 ultimately have a desirable enhanced red reflex attained while minimizing exposure to potentially harmful blue light.

Referring to FIG. 2, a target eye 30 is shown undergoing a representative eye surgery performed with red reflex-enhancing, eye safe assistance of the system 70. As part of such a system 70-assisted eye surgery, the target eye 30 is illuminated by warm white light (arrow WL), which is directed onto, and ultimately into, the target eye 30 by the lighting source 35. The lighting source 35 may be embodied as a lamp, e.g., a light-emitting diode (LED)-based, halogen-based, or other suitably configured lighting source that is coupled to or integral with the ophthalmic microscope 16 shown in FIG. 1. In a possible embodiment, the warm white light (arrow WL) is "warm" in the sense of having a color temperature of less than about 4000° K, with color temperatures falling slightly outside of this range being possible in other embodiments, e.g., up to about 4500° K.

The system 70 in the illustrated embodiment also includes the digital camera 36, which is operable for collecting digital images of the target eye 30 under illumination conditions using the warm white light (arrow WL). In an exemplary embodiment, the digital camera 36 may be a high-dynamic range (HDR) digital camera of the above-noted microscope 16 shown in FIG. 1. Thus, components of the system 70 may be integral with the microscope 16, i.e., an assembled internal or attached external component thereof, with the process steps of the method 50 of FIG. 4 being programmed functionality of the microscope 16. Other embodiments may be realized in which instructions embodying the method 50 are recorded on a non-transitory computer-readable medium, e.g., in memory 54 of the ECU 50C, and executed by the processor 52 of the ECU 50C as shown, or a processor 52 located apart from the ECU 50C in other embodiments, so as to enable the ECU 50C or processor 52 to cause the disclosed actions of the system 70 to occur. As noted above, the processor 52 in alternative embodiments may be integrated into other hardware, e.g., the microscope 16 and/or the digital camera 36, with inclusion of the processor 52 in the construction of the ECU 50C being non-limiting.

During predetermined stages of the representative eye surgery during which the surgeon desires to test and evaluate the red reflex of the target eye 30, the processor 52 causes the lighting source 35 to emit the warm white light (arrow WL), which may entail simply turning on the lighting source 35 at the onset of the surgery. At the same time, the processor 52 commands the digital camera 36, e.g., via corresponding camera control signals (arrow $CC_{36}$), to collect the digital image data (arrow 38). The collected digital image data (arrow 38) is communicated over transfer conductors or wirelessly to the processor 52 for execution of the various digital image processing steps embodying the method 50.

When selectively enhancing the red reflex of the target eye 30 as part of the present method 50, the processor 52 ultimately outputs a video display control signal (arrow $CC_{20}$) to the display screen(s) 20 and/or 200 to thereby cause the display screen(s) 20 and/or 200 to display a magnified dynamic image of the target eye 30 as set forth below. At other times when the red reflex is not being evaluated, the digital camera 36 may be used as needed to image the target eye 30, with possible illumination using light from other parts of the electromagnetic spectrum as needed in the surgeon's discretion.

The ECU 50C is depicted schematically in FIG. 2 as a unitary box solely for illustrative clarity and simplicity. Implemented embodiments of the ECU 50C may include one or more networked computer devices each with the processor(s) 52 and sufficient amounts of memory 54, the latter including a non-transitory (e.g., tangible) medium on which is recorded or stored a set of computer-readable instructions embodying the method 50 ("RR-Algo") readable and executable by the processor 52. A graphical user interface (GUI) device 60 may be used to facilitate intuitive interactions of the surgeon and attending surgical team with the system 70, with possible use cases detailed below. The memory 54 may take many forms, including but not limited to non-volatile media and volatile media. Instructions embodying the method 50 may be stored in memory 54 and selectively executed by the processor 52 to perform the various functions described below. The ECU 50C, either as a standalone device or integrated into the digital camera 26 and/or the microscope 16, may also include resident machine vision/motion tracking logic 58 ("Vision-Track") for tracking the target eye 30 and possibly performing other tasks, like identifying a surgical tool and/or the surgeon, which occurs during the course of eye surgery as set forth below.

As will be appreciated by those skilled in the art, non-volatile media may include optical and/or magnetic disks or other persistent memory, while volatile media may include dynamic random-access memory (DRAM), static RAM (SRAM), etc., any or all which may constitute a main memory of the ECU 50C. The input/output (I/O) circuitry 56 may be used to facilitate connection to and communication with various peripheral devices used during the surgery, inclusive of the digital camera 36, the lighting source 35, and the high-resolution display screen(s) 20 and/or 200. Other hardware not depicted but commonly used in the art may be included as part of the ECU 50C, including but not limited to a local oscillator or high-speed clock, signal buffers, filters, amplifiers, etc.

Referring now to FIG. 3, operation of the system 70 involves illumination of the target eye 30 with the warm white light (arrow WL), as noted generally above, with the warm white light (arrow WL) being directed onto/into the target eye 30 by the lighting source (L) 35, e.g., directly or using polarization. The incident warm white light (arrow WL) enters the target eye 30 through the dilated pupil 300 and reflects off of a surface of the retina 18 at the posterior of the vitreous chamber 21 or FIG. 2, as understood in the art. The reflected light (arrow $WL_R$) may be redirected via a mirror 39 toward an emission filter 40. The emission filter 40 in turn redirects the reflected light (arrow $WL_R'$) toward a prepositioned set of photosensors 42 in wired or wireless communication with the above-described ECU 50C or processor(s) 52. The emission filter 40 and the photosensors 42 may be integral with the digital camera 36 in some embodiments, or the emission filter 40 may be externally positioned as shown for illustrative clarity in FIG. 3.

As part of the present approach, the processor 52 is configured to detect a predetermined stage of eye surgery requiring detection of the red reflex, either at the sole discretion of the surgeon or, in other embodiments, as assisted by detection capabilities or machine learning assistance of the ECU 50C. For instance, the exemplary ECU 50C of FIGS. 1-3 may be operatively connected to the GUI device 60, such that identifying the predetermined stage of the eye surgery possibly includes receiving an input signal (arrow $CC_{60}$) from the GUI device 60. In such an embodiment, the input signal (arrow $CC_{60}$), shown as a two-way signal to indicate two-way handshake communication, is indicative of the predetermined stage of the eye surgery. A surgeon may interact with the display screen 20 or 200, itself optionally configured as a capacitive touch surface, to manually input the predetermined stage of the eye surgery. Alternatively, the ECU 50C or processor(s) 52 may determine an identity of a surgeon performing the eye surgery, such as using machine learning, e.g., neural networks to recognize particular behavioral patterns in the course of surgery. In such an embodiment, the input signal (arrow $CC_{60}$) is indicative of the identity of the surgeon.

When detection of the red reflex is desired, the processor(s) 52 may be used to track motion of the target eye 30 using the digital camera 36 and the resident motion tracking logic 58, with operation of the digital camera 36 controlled via camera control signals (arrow $CC_{36}$). As shown in FIG. 3, the target eye 30 during surgery has a dilated pupil 300 surrounded by an iris region 350, which in turn is surrounded by the sclera or whites of the target eye 30. The pupil 300 and directed of gaze of the target eye 30 may be detected and tracked in real time by the processor 52 using the logic 58 of FIG. 2, as understood in the art, with such tracking indicated in FIG. 3 by a tracking circle 300-T.

Figure 4:
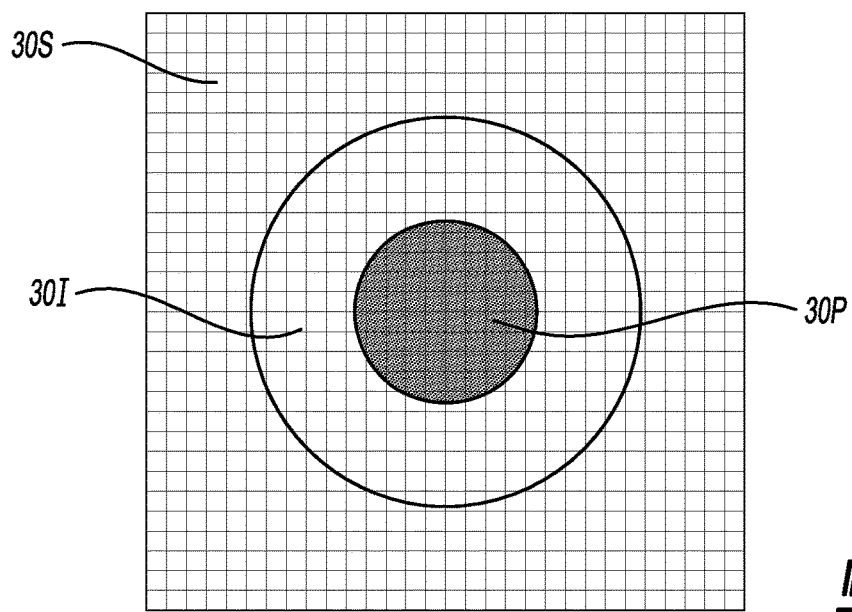
FIG. 4 shows a pixel image of a target eye with separate pupil and iris pixel regions.

Referring briefly to FIG. 4, within the collected digital images 19 of the target eye 30, as constructed from the digital image data (arrow 38) transmitted to the processor 52 during the predetermined stage of the eye surgery, the processor 52 digitally isolates a pupil pixel region 30P from an iris pixel region 30I surrounding the pupil pixel region 30P. As used herein, the pupil pixel region 30P corresponds to image pixels that coincide with imaged surface area of the pupil 300 of FIG. 3. Likewise, an iris pixel region 30I corresponds to image pixels coinciding with images surface area of the iris region 350 of FIG. 3, and possibly of the surrounding sclera 400, e.g., as a sclera pixel region 30S. Thereafter, the processor 52 adjusts a characteristic of constituent pixels comprising the pupil pixel region 30P or the iris pixel region 30I, or possibly both, in different manners, to thereby generate adjusted image data having a digitally enhanced red reflex.

This may occur based on the predetermined stage of the eye surgery, or adjusting the characteristic of the constituent pixels may occur based on the identity of the surgeon. For example, the processor 52 may learn a lighting preference of the surgeon over time, e.g., using a neural network or other suitable machine learning algorithm(s), and generate the input signal (arrow $CC_{60}$) via the processor 52, alone or using the GUI device 60, based at least in part on the lighting preference. Using an illustrative use scenario, for instance, if "Surgeon A" consistently demonstrates a particular lighting preference over N prior surgeries, the ECU 50C may register Surgeon A's preference in memory 52, relative to a different surgeon ("Surgeon B"), and thereafter implement the lighting preference during surgery N+1 without requiring any affirmative response or input from the surgeon. The processor 52 then outputs the video display control signal (arrow CC 20) to the display screen 20 and/or 200, as shown in FIG. 3, to cause the display screens 20 and/or 200 to display the adjusted images during the predetermined stage of the eye surgery.

Referring to FIG. 5, a non-limiting embodiment of the method 50 may be used for selectively enhancing the red reflex response of the target eye 30 (FIGS. 2 and 3) during eye surgery while at the same time minimizing exposure to blue light. As noted above, the present teachings are particularly well suited for use in certain stages of cataract surgery, such as incision and cataract removal stages of a typical cataract surgery. As noted above, aspects of the present teachings may be applied to other types of microsurgeries or other medical procedures where reduced exposure of human tissue to incident blue light would be beneficial.

When used to optimize surgical and patient health outcomes of ophthalmic procedures in particular, the method 50 combines the use of eye-safe warm white light illumination with programmed digital image processing functionality of the ECU 50C or processor 52 in order to, while at the same time creating an ideal, realistic digital rendering and projection of the surgical scene via the selectively adjusted images.

An exemplary embodiment of the method 50 commences with block B51 with illumination and imaging of the target eye 30, as best depicted in FIG. 3. Block B51 includes collecting digital images of the target eye 30 using the digital camera 36 as the target eye 30 is illuminated by warm white light (arrow WL). When the digital camera 36 is embodied as or includes an HDR digital camera, e.g., as an integral component of the microscope 16 of FIG. 1, collection of the digital image data (arrow 38 of FIG. 2) may include collecting three-dimensional HDR images of the target eye 30.

As part of block B51, the warm white light (arrow WL of FIGS. 2 and 3) may be directed onto/into the target eye 30 by the lighting source 35 shown in FIG. 2, either coaxially or obliquely, possibly using polarization techniques as appreciated in the art. The lighting source 35 may be an integral component of the microscope 16 in certain configurations. In some implementations of the method 50, the warm white light (arrow WL) has a color temperature of less than about 4000° K, with a color temperature ranges greater than 4000° K being possible in other embodiments. However, as reduced exposure to blue light is a goal of the method 50, most or substantially all of the constituent light used as the warm white light (arrow WL) should be comprised of light falling within the red spectrum, e.g., 620 nm to 750 nm, and/or the orange spectrum, e.g., 590 nm to 620 nm, as opposed to full spectrum light.

One approach to implementing block B51 is to control the spectrum of light emitted by the lighting source 35 so that the emitted light includes more red wavelengths. The warmer light then produces a higher red reflex. Alternatively, one may implement an excitation optical filter 37 after the lighting source 35 to block blue and green wavelengths, thereby increasing the red wavelength ratio. Such an approach enables use of a cool lighting source 35, then blocking blue light (e.g., 400-500 nm) and some green light (e.g., 500-600 nm) via the excitation optical filter 37. The resulting spectrum would have a greater red wavelength content, thus providing the intended warm white light (arrow WL). The method 50 thereafter proceeds to block B53.

Block B53 includes detecting the redirected reflected light (arrow $WL_R'$ of FIG. 3) using digital camera 36, and in particular using the photosensors 42 thereof. Possible embodiments of the photosensors 42 include photon detectors in the form of, e.g., photovoltaic cells, photoelectric sensors, phototubes, or other application suitable photodetectors. Within a typical digital camera construction, for example, a charge-coupled device (CCD) or complementary metal-oxide semiconductor (CMOS) integrated circuit may be used to process detected photons of the redirected reflected light (arrow $WL_R'$) into corresponding electronic signals. The processed readings from the photosensors 42 are ultimately transmitted as the image data (arrow 38) to the ECU with the method 50 thereafter proceeding to block B54.

Block B54 includes identifying, via the processor 52 in communication with the digital camera 36, a predetermined stage of eye surgery requiring or benefitting from detection of the red reflex. To this end, the processor 52 of FIGS. 1-3 may be operatively connected to the GUI device 60 shown in FIGS. 2 and 3, such that identifying the predetermined stage of the eye surgery may include receiving the input signal (arrow $CC_{60}$) from the GUI device 60, with the input signal (arrow $CC_{60}$) possibly being indicative of the predetermined stage of the eye surgery.

Alternatively, the processor 52 may optionally identify a surgeon performing the eye surgery, in which case the input signal (arrow $CC_{60}$) is indicative of the identity of the surgeon. Illustrative example approaches for identifying the surgeon include registering actions of the surgeon, such as touching an icon on the GUI device 60 to select the surgeon's name from a displayed listing of surgeon names, or automatically identifying the surgeon using machine vision/facial recognition software. Other possible embodiments include learning a lighting preference of the surgeon over time via the processor 52, e.g., using a neural network or other machine learning algorithm(s), and then generating the input signal (arrow $CC_{60}$) via the processor 52 based on the identity of the surgeon and the surgeon's demonstrated lighting preference.

Identifying the predetermined stage of the eye surgery in some implementations of the method 50 may include detecting a surgical tool via the processor 52 50C, e.g., using the digital camera 36 and associated machine vision logic. Such logic may be part of the tracking logic 58 or a separate algorithm configured to detect and identify the surgical tool based on its shape and size. The processor 52 may then automatically detect the predetermined stage of the eye surgery based on the identity of the surgical tool. The method 50 proceeds to block B55 when the predetermined stage of the eye surgery is detected by any of the above-noted techniques or other suitable means. The method 50 proceeds in the alternative to block B56 when the processor 52 does not detect the predetermined stage of the eye surgery.

At block B55, the processor 52 digitally isolates the pupil pixel region (PPR) from the iris pixel region 30I surrounding the PPR 30P, with such regions illustrated in FIG. 4. As part of block B55, the processor 52 alone or using associated functions of the ECU 50C may track motion of the target eye 30 using the digital camera 36 and the above-noted motion tracking logic 58. As is well understood in the art of artificial intelligence, eye tracking algorithms are commonly used to detect and track a user's gaze direction, and to transform the resulting detection data, such as an estimated optical axis, into a relevant frame of reference. In the present method 50, the relevant frame of reference includes a plane of constituent image pixels constituting the various digital images described by the collected image data (arrow 38). By tracking the motion of the pupil 30O of FIG. 3 and mapping the corresponding pixel locations thereof, the processor 52 is able to track motion of the target eye 30 in real time, such that the pupil pixel region remains identifiable within the displayed images throughout the course of the eye surgery. The method 50 proceeds to block B57 once the processor 52 has digitally isolated the pupil pixel region 30P.

Block B56 may entail performing a default image processing algorithm on a full digital image of the target eye 30, inclusive of the pupil pixel region 30P and the iris pixel region 30I, and possibly inclusive of imaged regions lying outside of the iris pixel region 30I. When execution of block B54 leads to a decision that the red reflex is not required, in other words, the full digital image(s) may be treated using the default image processing algorithm, with automatic white balancing (AWB) being one possible default solution.

As appreciated in the art, AWB algorithms automatically correct for ambient lighting conditions when producing a more naturally appearing digital image. A typical AWB algorithm estimates the illuminant of an imaged scene in the form of a pixel image, and thereafter corrects the color balance within the pixel image. For example, color balance correction may entail using automatic or user-selected histogram adjustments to discard certain pixel colors at extreme ends of the red, green, and blue histogram spectrum, and then stretching the remaining ranges. Other approaches include averaging respective hues of the brightest and darkest pixels in the image, or applying a weighted function. The method 50 proceeds to block B60 once the default algorithm has been applied.

At block B57, the ECU 50C next determines whether gain adjustment is required within the pupil pixel region 30P. Possible approaches to implementing block B57 include allowing the surgeon, e.g., via the GUI device 60 of FIG. 3, to select gain adjustment as an option, such as by touching a corresponding icon on a touch sensitive screen of the GUI device 60. Alternatively, the processor 52 may process the brightness, color, or other characteristics of a full image of the target eye 30, as collected at block B51, to determine whether improved red reflex contrast could be best attained via processing of the pupil pixel region 30P, the iris pixel region 30I, or both. The processor 52 may compare the spectral content of the constituent pixels of the respective pupil and iris pixel regions 30P and 30I to each other and/or threshold values as part of block B57. The method 50 proceeds to block B58 when gain adjustment to constituent pixels of the pupil pixel region 30P is required. Otherwise, the method 50 proceeds to block B59.

At block B58, the processor 52 adjusts a characteristic of constituent pixels comprising the pupil pixel region 30P to selectively enhance the red reflex. As part of block B58, for instance, the processor 52 may increase digital gains as the characteristic, with adjustment in this instance being solely of the constituent pixels of the pupil pixel region 30P. As understood in the art of digital image processing, analog gain adjustments may be employed, e.g., at block B53, in order to adjust detection sensitivity, typically by amplifying or dampening a corresponding voltage generated by each photon detected by the photosensors 42 of FIG. 2. In contrast to analog gain adjustments, the digital gain adjustments employed in block B58 are used to adjust pixel values after such voltages have been read and digitized. The method 50 proceeds to block B61 once the digital gains have been boosted in the pupil pixel region 30P.

Block B59 includes adjusting a characteristic of constituent pixels comprising the iris pixel region 30I, such as by applying a white balance algorithm solely to the constituent pixels of the iris pixel region 30I. Image processing algorithms concurrently or alternatively conducted at block B59 may include tone mapping, which compresses tonal values of a high dynamic range image into a lower range. The method 50 then proceeds to block B61.

At block B60, the processor 52 displays the non-adjusted image data (arrow 38) via the display screen 20 and/or 200 of FIG. 1. Block B60 is performed via transmission of the video display control signal (arrow CC 20 of FIG. 2) to the display screens 20 and/or 200 to cause illumination of thereof with the displayed magnified images of the target eye 30. The method 50 then returns to block B51.

Block B61 includes displaying an adjusted image via the display screen. The content of the displayed image will vary depending on whether block B61 is reached from block B58, in which the processor 52 boosts the digital gain in the pupil pixel region as described above, or from block B59 where the processor 52 applies a white balancing algorithm or other suitable image processing technique(s) to portions of the digital image lying outside of the pupil pixel region. The method 50 then returns to block B51.

The present teachings as set forth above combine warm white light illumination and selective digital image processing during cataracts removal, lens replacement, and other surgeries of the eye in order to reduce the risk of blue light toxicity, as well as to selectively enhance the red reflex. The method 50 departs from the conventional practice of microscope-based illumination using broad spectrum light, or light falling within the daylight white range of wavelengths.

While digital color adjustment to a displayed image may be used to produce realistic looking surgical scenes under such broad spectrum or warm white light illumination conditions, light entering a patient's eye is unaffected, and thus contains high levels of blue wavelength light. Accordingly, conventional image color adjustment does not avoid the noted phototoxicity risks. Moreover, the present teachings are useful in selectively enhancing the red reflex during predetermined stages of surgery, automatically and thus unobtrusively to the surgeon. These and other benefits will be readily appreciated by those skilled in the art in view of the foregoing disclosure.

The detailed description and the drawings are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A method for enhancing a red reflex of an eye during an eye surgery, the method comprising:
   collecting digital image data of the eye during the eye surgery using a digital camera as the eye is illuminated by warm white light from a light source; and
   during a predetermined stage of the eye surgery:
      isolating a first pixel region from a second pixel region within the digital image data via a processor, wherein the first pixel region is a pupil pixel region and the second pixel region is an iris pixel region of a respective pupil and iris of the eye;
      selectively adjusting a characteristic of constituent pixels comprising the first pixel region or the second pixel region, via the processor, to thereby provide an enhanced first pixel region or an enhanced second pixel region as an enhanced red reflex; and
      transmitting a video display control signal to a digital display screen to thereby present an adjusted digital image of the eye having the enhanced red reflex.

2. The method of claim 1, illuminating the eye with light that is emitted by the light source, and wherein the light from the light source includes the warm white light.

3. The method of claim 2, wherein illuminating the eye with warm white light includes using an excitation filter to block blue and green wavelengths of the light that is emitted by the light source.

4. The method of claim 2, wherein illuminating the eye with the warm white light includes directing the warm white light onto the eye from an ophthalmic microscope, wherein the light source is an integral part of the ophthalmic microscope.

5. The method of claim 1, wherein the digital camera includes a high-dynamic range (HDR) digital camera, and wherein collecting digital images includes collecting three-dimensional HDR images of the eye via the HDR digital camera.

6. The method of claim 1, further comprising:
   identifying the predetermined stage of the eye surgery by detecting, via the processor using machine vision logic, a surgical tool used in the predetermined stage of the eye; and
   automatically detecting the predetermined stage of the eye based on an identity of the surgical tool.

7. The method of claim 1, further comprising:
   receiving, via the processor, and input signal indicative of an identity of a surgeon performing the eye surgery; and
   adjusting the characteristic of the constituent pixels via the processor based on a predetermined lighting preference of the surgeon based on the identity.

8. The method of claim 1, wherein adjusting the characteristic of the constituent pixels includes applying a white balance algorithm solely to the constituent pixels comprising the first pixel region or the second pixel region.

9. The method of claim 1, wherein adjusting the characteristic of the constituent pixels includes automatically increasing digital gains, via the processor, solely of the constituent pixels of the first pixel region or the second pixel region.

10. The method of claim 1, wherein isolating the first pixel region from the second pixel region includes automatically tracking motion of the eye during the eye surgery using the digital camera and motion tracking logic of the processor.

11. The method of claim 1, further comprising:
providing input signals from a graphical user interface (GUI) device to the processor, the input signals being indicative of the predetermined stage of the eye surgery requiring an enhanced red reflex of the eye; and
detecting the predetermined stage of the eye surgery via the input signals from the GUI.

12. A system for enhancing a red reflex of an eye during an eye surgery, comprising:
a lighting source operable for directing warm white light onto the eye, the warm white light having a color temperature of less than about 4500° K;
a graphical user interface (GUI) device configured to provide input signals indicative of a predetermined stage of the eye surgery, the predetermined stage of the eye surgery requiring an enhanced red reflex of the eye;
a digital camera operable for collecting digital images of the eye as the eye is illuminated by the warm white light; and
a processor in communication with the digital camera and the GUI, wherein the processor is configured to:
detect, using the input signals from the GUI, the predetermined stage of the eye surgery requiring the enhanced red reflex;
automatically track motion of the eye using the digital camera and motion tracking logic;
within the digital images of the eye during the predetermined stage of the eye surgery, digitally isolate a pupil pixel region from an iris pixel region surrounding the pupil pixel region;
adjust a characteristic of constituent pixels comprising the pupil pixel region or the iris pixel region, in response to the input signals from the GUI, to thereby generate adjusted images having the enhanced red reflex; and
output a video display control signal to one or more display screens to thereby cause the one or more display screens to display the adjusted images having the enhanced reflex during the predetermined stage of the eye surgery.

13. The system of claim 12, further comprising the one or more display screens.

14. The system of claim 12, wherein the lighting source includes a lamp coupled to or integral with an ophthalmic microscope.

15. The system of claim 14, wherein the digital camera includes a high-dynamic range (HDR) digital camera of the ophthalmic microscope.

16. The system of claim 12, further comprising:
an excitation filter configured to block blue and green wavelengths of light emitted by the light source to thereby produce the warm white light.

17. The system of claim 12, wherein the processor is configured to determine an identity of a surgeon performing the eye surgery, and wherein the input signals are indicative of the identity of the surgeon, such that the processor is configured to adjust the characteristic of the constituent pixels based on the identity of the surgeon.

18. The system of claim 12, wherein the processor is configured to adjust the characteristic of the constituent pixels in response to the input signals by applying a white balance algorithm solely to the constituent pixels of the iris pixel region.

19. A tangible, non-transitory computer-readable medium on which is recorded instructions for enhancing a red reflex response of an eye during an eye surgery, wherein execution of the instructions by a processor causes the processor to:
receive digital images of the eye from a digital camera in communication with the processor as the eye is illuminated by warm white light from an ophthalmic microscope, the warm white light having a color temperature of less than about 4500° K;
providing input signals to the processor via a graphical user interface (GUI) device, wherein the input signals are indicative of a predetermined stage of the eye surgery requiring detection of an enhanced red reflex;
within the digital images of the target eye, isolate a pupil pixel region from an iris pixel region surrounding the pupil pixel region during the predetermined stage of the eye surgery requiring detection of the enhanced red reflex;
adjust a characteristic of constituent pixels comprising the pupil pixel region or the iris pixel region, in response to the input signals from the GUI, to thereby generate adjusted images having the enhanced red reflex, including applying a white balance algorithm solely to the constituent pixels of the iris pixel region or automatically increasing digital gains solely of the constituent pixels of the pupil pixel region; and
transmit a video display control signal to at least one display screen to thereby cause the at least one display screen to display the adjusted images during the predetermined stage of the eye surgery.

20. The computer-readable medium of claim 19, wherein execution of the instructions by the processor causes the processor to:
command a light source to illuminate the eye with light; and
command an excitation optical filter to block blue and green wavelengths of the light from the light source to thereby output the warm white light.

* * * * *